United States Patent [19]
Pilgram et al.

[11] Patent Number: 4,554,283
[45] Date of Patent: Nov. 19, 1985

[54] APHICIDAL 3-(2-ALKYL-2,3-DIHYDROBENZOFURAN-7-YL)-5-(R,R$^1$-AMINO)-1,3,4-OXADIAZOL-2(3H)-ONES

[75] Inventors: Kurt H. Pilgram; Richard D. Skiles, both of Modesto, Calif.

[73] Assignee: Shell Oil Company, Houston, Tex.

[21] Appl. No.: 643,331

[22] Filed: Aug. 22, 1984

[51] Int. Cl.$^4$ ............... A01N 43/82; C07D 413/10
[52] U.S. Cl. .................... 514/364; 534/560; 548/144; 549/462
[58] Field of Search ............ 548/144; 514/364

[56] References Cited

U.S. PATENT DOCUMENTS 4,269,846  5/1981  Huang et al. .................. 514/364
4,406,910  9/1983  Pilgram et al. ................ 548/144

FOREIGN PATENT DOCUMENTS 887147   7/1981  Belgium .
 48040   3/1982  European Pat. Off. .
194870  11/1983  Japan .
222083  12/1983  Japan .

Primary Examiner—Alton D. Rollins

[57] ABSTRACT

Certain aphicidal 3-(2-alkyl-2,3-dihydrobenzofuran-7-yl)-5-(R,R$^1$-amino)-1,3,4-oxadiazol-2(3H)-ones.

2 Claims, No Drawings

APHICIDAL 3-(2-ALKYL-2,3-DIHYDROBENZOFURAN-7-YL)-5-(R,R¹-AMINO)-1,3,4-OXADIAZOL-2(3H)-ONES

DESCRIPTION OF THE INVENTION

It has been found that certain 3-(2-alkyl-2,3-dihydrobenzofuran-7-yl)-5-(R,R¹-amino)-1,3,4-oxadiazol-2(3H)-ones are toxic with respect to aphids that feed upon plants.

These aphicides are described by the generic formula:

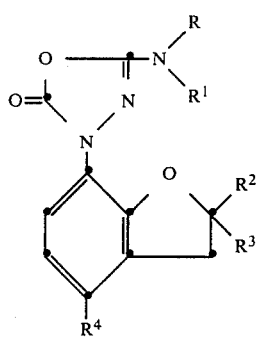

wherein R is alkyl of one to three carbon atoms; $R^1$ is hydrogen or alkoxy of one to three carbon atoms; $R^2$ is alkyl of one to three carbon atoms; $R^3$ and $R^4$ each is hydrogen or alkyl of one to three carbon atoms.

In these compounds, each alkyl and alkoxy moiety suitably is straight-chain or branched-chain in configuration. Preferably, each alkyl moiety is methyl, and any alkoxy moiety is methoxy.

The compounds of Formula I wherein $R^3$ is hydrogen exist in the form of optical isomers. The isomeric forms have not been separated and isolated. This invention contemplates all of the aphicidally active isomers, as well as mixtures containing them, whether resulting from the method of preparation, or deliberately prepared.

Compounds of Formula I are formed in two ways, depending upon the reactivity of the precursor 1-(2-alkyl-2,3-dihydrobenzofuran-7-yl)-4-alkoxy-4-alkylsemicarbazide (II) with phosgene.

In one case, exemplified in Example 3, hereinafter, the treatment leads directly to the compound of Formula I wherein $R^1$ is alkoxy,

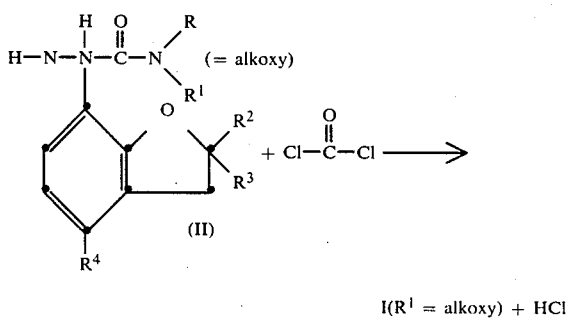

Treatment of that product with Hunig's base (N,N-diisopropyl-N-ethylamine) gives in part the corresponding compound wherein $R^1$ is hydrogen (Example 4, hereinafter).

Treatment of II with phosgene is carried out in the presence of a suitable inert solvent, such as benzene. The cyclization occurs in some cases when the treatment is carried out at room temperature, and in most cases when it is carried out at a moderately higher temperature.

In other cases, and/or where the treatment is carried out at lower temperatures, cyclization does not occur, but instead the corresponding 1-chlorocarbonyl-1-(2-alkyl-2,3-dihydrobenzofuran-7-yl)-4-alkoxy-4-alkyl-semicarbazide (III) is formed

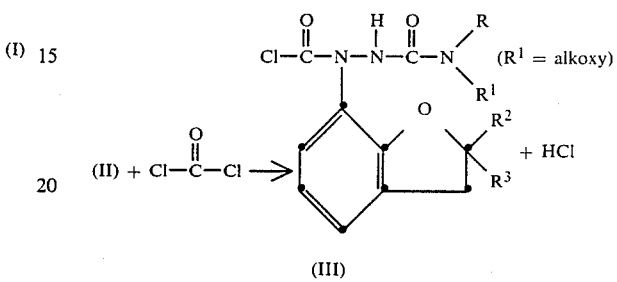

Treatment of III with Hunig's base gives I, as a mixture of the species wherein $R^1$ is hydrogen and the species wherein $R^1$ is alkoxy.

Treatment of I ($R^1$ = alkoxy) or III with Hunig's base is conducted in methanol at a moderately elevated temperature, conveniently the boiling point of methanol.

The precursors of Formula II can be prepared by treating the appropriate 7-hydrazino-2,3-dihydrobenzofuran (IV) with the appropriate N-alkoxy-N-alkylcarbamic chloride in the presence of a tertiary amine as hydrogen chloride acceptor. The reaction proceeds according to the equation:

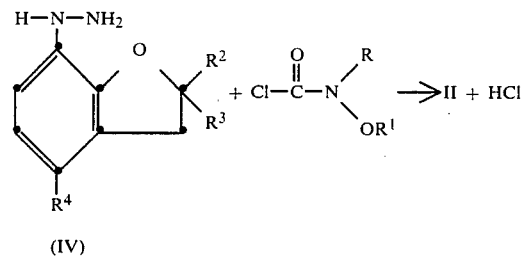

This reaction can be effected by slowly adding one of the reagents to a stirred solution of the other reagent in an inert solvent (tetrahydrofuran is a typical example) in the presence of the amine at a low temperature—for example −5° C. to 0° C., then if necessary warming the mixture or even heating it at reflux temperature for a time sufficient to ensure completion of the reaction. The formula I species is isolated from the reaction mixture, and purified, by conventional means, as is shown in particular instances in the Examples, hereinafter. The N-alkoxy-N-alkylcarbamic chlorides are known and readily available materials. A suitable hydrogen chloride acceptor in many instances is N,N-diisopropyl-N-ethylamine; triethylamine and pyridine are also suitable.

The 7-hydrazino-2,3-dihydrobenzofuran (IV) is prepared from the corresponding 7-nitro-2,3-dihydrobenzofuran (V) according to the reactions expressed by the equations A—NO₂(V)→A—NH₂(VI)→A—N=N—SO₃Na(-VII)→A—NHNHSO₃K(VIII)→IV wherein A represents

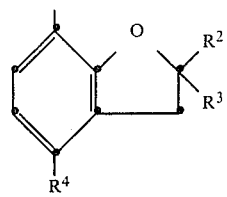

Intermediate VI is prepared by conventional Raney nickel-catalyzed hydrogenation in a Parr shaker of a solution of intermediate V in an inert solvent such as tetrahydrofuran. Intermediate VII is prepared by diazotizing intermediate VI, followed by treatment with sodium sulfite. The diazotization is conventional, effected by treating VI with concentrated hydrochloric acid at about room temperature, diluting the mixture with water, cooling it to about 0° C. and slowly adding an aqueous solution of sodium nitrite to the stirred mixture. Then the diazonium salt solution is added to a cold aqueous solution/suspension of sodium sulfite, and the mixture is stirred at room temperature to complete the reaction. Intermediate VII may be isolated and further treated, or the crude product may be used to prepare intermediate VIII. In either case, aqueous VII is treated with sodium dithionite (added in portions to the stirred mixture at room temperature), then potassium chloride is added and the mixture is stirred at a moderately elevated temperature (for example, 60°–80° C.) for a time sufficient to complete the reaction. Intermediate VIII is recovered as a solid by filtering the mixture. VIII then can be converted to intermediate IV by mixing it with a lower alkanol, such as methanol, treating the cold (0° C.) mixture with hydrogen chloride, evaporating the alkanol, treating the residue with aqueous sodium hydroxide, and extracting the resulting IV, using a suitable solvent.

The 7-nitro-2,3-dihydrobenzofuran precursor (V) can be prepared from the appropriate 2-nitrophenol by the general procedures described in U.S. Pat. Nos. 3,412,110 and 4,406,910 for the preparation of similar 2,3-dihydrobenzofurans: an alkali metal (M) salt of the phenol (IX) is treated with the appropriate 3-halo-1-alkene, the resulting 1-(2-alken-1-yloxy)-2-nitrobenzene (X) is Claisen-rearranged to form the corresponding 2-(2-alken-1-yl)-6-nitrophenol (XI), which is ring-closed to form the 7-nitro-2,3-dihydrobenzofuran precursor (V).

The reactions proceed according to the equations:

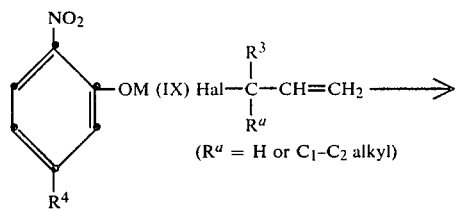

($R^a$ = H or $C_1$-$C_2$ alkyl)

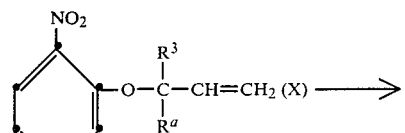

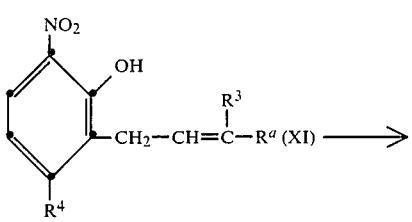

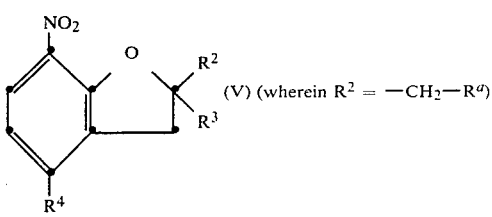

(V) (wherein $R^2$ = —$CH_2$—$R^a$)

Conversion of IX to X can be effected by treating a solution of the phenol (IX), in a solvent such as dimethyl sulfoxide, with an alkali metal base such as sodium hydroxide or sodium hydride, in the presence of, or subsequently treating the alkali metal phenoxide thus formed with the appropriate alkenyl halide, then heating the resulting mixture at a moderately elevated temperature, for example, 80°–120° C.

Claisen-rearrangement of X is effected conventionally—conveniently by heating X to a moderately elevated temperature—e.g., 150°–250° C.—in an inert atmosphere.

Ring closure of XI is effected by heating it in the presence of an acid. Suitable acids include the mineral acids, such as hydrochloric, hydrobromic, sulfuric and phosphoric acids. The hydrohalide acids are to be preferred since they have less tendency to cause side-reactions. An organic acid such as acetic acid can also be utilized—and may be used as reaction medium when a mineral acid is used. Ordinarily, the acid is employed as an aqueous solution.

It must be noted that in some cases hydrobromic acid will not be suitable, because at least in part it will add to the double bond, giving the bromoalkyl derivative rather than effecting the cyclization. In such a case, cyclization can be effected by use of a less-reactive acid, such as hydrochloric acid.

The preparation, isolation and physical properties of typical individual species of the compounds of Formula I, in particular instances, are described in the following examples. The identity of each product, and each of the intermediates involved, was confirmed by appropriate chemical and spectral analyses.

EXAMPLE 1

3-(2,3-Dihydro-2-methylbenzofuran-7-yl)-5-(methylamino)-1,3,4-oxadiazol-2(3H)-one (1)

3-(2,3-Dihydro-2-methylbenzofuran-7-yl)-5-(N-methoxy-N-methylamino)-1,3,4oxadiazol-2(3H)-one (2)

A solution of 64 g of sodium hydroxide in 75 ml of water was added drop-to-drop (over 15 minutes) to a stirred mixture of 209.6 g of 2-nitrophenol, 115.5 g of 3-chloropropene and 500 ml of dimethyl sulfoxide (DMSO), at room temperature. The mixture was stirred at 85°-90° C. for 18 hours and then mixed with 3 liters of water. The resulting mixture was extracted with methylene chloride, the extract was washed with ice water, dried (MgSO$_4$) and the solvent was evaporated, to give 1-(2-propen-1-yloxy)-2-nitrobenzene (1A), as an amber syrup.

A mixture of 265 g of 1A and 30 g of magnesium chloride was stirred at 190°±4° C. for 2.5 hours, then cooled and mixed with 500 ml of ether. The resulting mixture was washed with cold water. The ether phase was separated, dried (MgSO$_4$) and the solvent was evaporated. The residue was vacuum distilled in a Vigreaux column to give an oil, b.p.: 123°-127° C., 0.15 Torr., that solidified on standing, m.p.: 70°-72° C., identified as 2,3-dihydro-2-methyl-7-nitrobenzofuran (1B).

A mixture of 81 g of 1B, 400 ml of tetrahydrofuran (THF) and 3 g of activated Raney nickel catalyst was shaken under 35 p.s.i.g. hydrogen pressure at room temperature for 4 hours. The resulting mixture was treated with 20 g of magnesium sulfate, filtered and the solvent was evaporated from the filtrate, to give 7-amino-2,3-dihydro-2-methylbenzofuran (1C), as an amber syrup.

A mixture of 157 ml of concentrated hydrochloric acid and 66.1 g of 1C was stirred at room temperature for one hour, then 485 ml of water was added. The mixture was warmed to 70° C., then allowed to cool and stand at room temperature for 18 hours, then cooled to 5° C. while a solution of 33.7 g of sodium nitrite in 48 ml of water was added drop-by-drop (over 20 minutes). The resulting solution was stirred at 5° C. for 1 hour, then added drop-by-drop (over 10 minutes) to a stirred mixture of 393.5 g of sodium sulfite in 755 ml of water, at 5° C. The resulting mixture was stirred at room temperature for 2 hours, then a slurry of 77.2 g of sodium dithionite in 100 ml of water was added, in portions, to the stirred mixture. The mixture was stirred for 2 hours at room temperature, then at 70° C. for 15 minutes, when 1 pound of potassium chloride was added. The mixture was stirred at room temperature for 18 hours, cooled to 4° C. and filtered. 125 g of the resulting solid product was mixed with 500 ml of methanol. The resulting suspension was stirred at 0° C. while an excess of anhydrous hydrogen chloride was added. The mixture was stirred for 1 hour at 0° C., then most of the methanol was evaporated under reduced pressure at room temperature. The mixture was mixed with 500 ml of cold water, made basic by addition of 50% aqueous sodium hydroxide solution, and extracted with ether. The extract was dried (MgSO$_4$) and the solvent was evaporated to give 7-hydrazino-2,3dihydro-2-methylbenzofuran (1D), as an amber syrup.

4.9 g of N-methoxy-N-methylcarbamic chloride was added, drop-by-drop (over 5 minutes) to a mixture of 6.6 g of 1D, 125 ml of THF and 5.2 g of N,N-diisopropyl-N-ethylamine, at −10° C. The mixture was stirred for 1 hour at 0° C., and then mixed with ice water. The resulting mixture was extracted with ether, and extract was dried (MgSO$_4$), filtered and the solvent was evaporated, to give 1-(2,3-dihydro-2-methylbenzofuran-7-yl)-4-methoxy-4-methylsemicarbazide (1E), as an amber syrup.

3.0 g of 1E was added to a stirred solution of 75 ml of 12.5% phosgene in benzene. The resulting mixture was stirred for 2 hours at room temperature, then the solvent was evaporated to give 1-(chlorocarbonyl)-1-(2,3-dihydro-2-methylbenzofuran-7-yl)-4-methoxy-4-methylsemicarbazide (1F), as an amber syrup.

3.4 g of 1F, 2.5 g of N,N-diisopropyl-N-ethylamine and 75 ml of methanol were mixed. The resulting solution was allowed to stand at room temperature for 18 hours, then was warmed on a steam bath for 24 hours. The solvent was evaporated under reduced pressure and the residue was flash chromatographed over silica gel, a 2:15:33 v:v:v mixture of tetrahydrofuran, ethyl acetate and hexane being used as eluent. One product, R$_f$=0.14, was obtained as an off-white solid. Recrystallization from ether/hexane gave 2, m.p.: 91°-93° C. A second product, R$_f$=0.17, was obtained as an off-white solid. Recrystallization from ether/hexane gave 1, m.p.: 147°-149° C.

EXAMPLE 2

3-(2,3-Dihydro-2,2,4-trimethylbenzofuran-7-yl)-5-(N-methoxy, N-methylamino)-1,3,4-oxadiazol-2(3H)-one (3)

3 was prepared, as an amber syrup, by treating 7-hydrazino-2,3-dihydro-2,2,4-trimethylbenzofuran (prepared by the method described in U.S. Pat. No. 4,406,910) according to the procedures described in Example 1 for preparing 1F from 1D.

EXAMPLE 3

3-(2,3-Dihydro-2,2,4-trimethylbenzofuran-7-yl)-5-(methylamino)-1,3,4-oxadiazol-2(3H)-one (4)

A solution of 3.0 g of 3, 75 ml of methanol and 1.3 g of N,N-diisopropyl-N-ethylamine was warmed on a steam bath for 18 hours. The solvent was evaporated under reduced pressure, the residue was mixed with 75 ml of water and the mixture was extracted with ether. The extract was dried (MgSO$_4$) and the solvent was evaporated under reduced pressure. The residue was flash-chromatographed over silica gel, using a 2:15:33 v:v:v mixture of THF, ethyl acetate and hexane as eluent. Two products were obtained: one, a light amber syrup, Rf=0.49, was identified as 3; the second, a solid (Rf=0.24) was recrystallized from ether to give 4, as a colorless solid, m.p.: 183°-184° C.

Compounds of Formula I are toxic to aphids that feed on plants, with little or no toxicity to other pests which feed on plants.

Accordingly, the invention includes a method for combatting plant-feeding aphids which comprises applying to the foliage of the plants to be protected an effective amount of a compound of Formula I.

For application, the compound of the invention ordinarily is applied most effectively by formulating it with a suitable inert carrier or surface-active agent, or both. The invention, therefore, also includes compositions suitable for combatting aphids, such compositions comprising an inert carrier or surface-active agent, or both, and as active ingredient at least one compound of the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wet-table powders, dusts, granules, solutions, emulsifiable concentrates, emulsions, suspension concentrates and aerosols. Wettable powders are usually compounded to contain 25-75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wet-table powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors, Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3-7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control aphids comprises applying the compound, ordinarily in a composition of one of the aforementioned types, to a locus or area to be protected from the mites, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the aphid contacts—is of the order of 0.001 to 0.5% based on the total weight of the formulation, though under some circumstances the effective concentration will be as little as 0.0001% or as much as 2%, on the same basis.

APHICIDAL ACTIVITY

Toxicity of compounds of this invention with respect to aphids was determined as follows:

Pea aphids (*Acyrthosiphon pisum* (Harris)) were tested by placing about 100 aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for each test compound.

In each set of tests, identical tests were conducted using Parathion as a standard for comparison.

In each instance, the toxicity of the test compound was compared to that of the standard pesticide (Parathion), its relative toxicity then being expressed in terms of the relationship between the amount of the test compound and the amount of the standard pesticide required to produce the same percentage (50%) of mortality in the mites. By assigning the standard pesticide an arbitrary rating of 100, the toxicities of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table I.

TABLE I

| Compound Number | Toxicity Index, Pea Aphids |
| --- | --- |
| 1 | 14 |
| 2 | 77 |
| 3 | 10 |
| 4 | 177 |

We claim:
1. A compound of the formula:

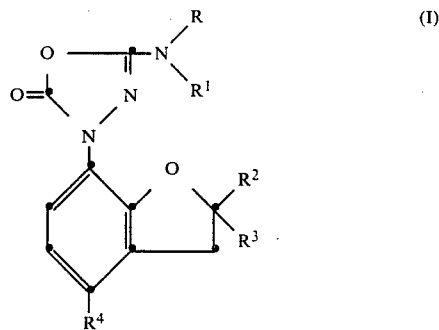

wherein R is alkyl of one to three carbon atoms; $R^1$ is hydrogen or alkoxy of one to three carbon atoms; $R^2$ is alkyl of one to three carbon atoms; $R^3$ and $R^4$ each is hydrogen or alkyl of one to three carbon atoms.

2. A method for protecting a plant from aphids which comprises applying to the plant an aphicidally effective dosage of a compound of claim 1.

* * * * *